United States Patent
Lai et al.

(10) Patent No.: US 6,805,712 B2
(45) Date of Patent: Oct. 19, 2004

(54) PROCESS FOR THE PRODUCTION OF POLYSILOXANE-BASED POLYMERIC COMPOSITIONS FOR USE IN MEDICAL DEVICES

(75) Inventors: Yu-Chin Lai, Pittsford, NY (US); Edmond T. Quinn, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/103,260

(22) Filed: Mar. 20, 2002

(65) Prior Publication Data

US 2003/0181588 A1 Sep. 25, 2003

(51) Int. Cl.$^7$ ............... A61F 2/14; C08L 83/04; C08G 77/06; C08G 77/20
(52) U.S. Cl. ............... 623/5.16; 264/1.32; 351/167; 523/113; 524/267; 524/268; 524/588; 525/478; 528/31; 528/32; 528/43
(58) Field of Search ............... 525/478; 524/257, 524/268, 588, 267; 528/31, 32, 43; 264/1.32; 351/167; 623/5.16; 523/113

(56) References Cited

U.S. PATENT DOCUMENTS

| | | | | |
|---|---|---|---|---|
| 3,996,187 A | | 12/1976 | Travnicek | 260/37 |
| 3,996,189 A | | 12/1976 | Travnicek | 260/37 |
| 4,077,943 A | * | 3/1978 | Sato et al. | 528/15 |
| 4,154,714 A | * | 5/1979 | Hockemeyer et al. | 524/268 |
| 4,304,895 A | * | 12/1981 | Loshaek | 526/313 |
| 4,380,367 A | * | 4/1983 | Suzuki | 385/141 |
| 4,418,165 A | | 11/1983 | Polmanteer et al. | 523/210 |
| 4,478,911 A | * | 10/1984 | Price | 428/332 |
| 4,647,282 A | | 3/1987 | Fedorov et al. | 623/4 |
| 4,868,251 A | | 9/1989 | Reich et al. | 525/479 |
| 5,441,690 A | * | 8/1995 | Ayala-Esquilin et al. | 264/277 |
| 5,444,106 A | * | 8/1995 | Zhou et al. | 523/107 |
| 5,512,609 A | | 4/1996 | Yang | 523/107 |
| 5,623,029 A | | 4/1997 | Yang | 525/478 |
| 5,739,370 A | * | 4/1998 | Razzano | 556/461 |
| 6,121,368 A | * | 9/2000 | Heying et al. | 524/493 |
| 6,415,093 B1 | * | 7/2002 | Nakamura et al. | 385/141 |
| 6,483,981 B1 | * | 11/2002 | Krahn et al. | 385/140 |
| 2002/0074086 A1 | * | 6/2002 | Nakamura et al. | 156/329 |
| 2002/0082691 A1 | | 6/2002 | Christ et al. | 623/6.56 |

FOREIGN PATENT DOCUMENTS

WO    WO 95/17460    6/1995

OTHER PUBLICATIONS

English Abstract of JP–10056588 Sep. 1998.

* cited by examiner

*Primary Examiner*—Jeffrey B. Robertson
(74) *Attorney, Agent, or Firm*—Rita D. Vacca

(57) ABSTRACT

A process for producing polysiloxane prepolymers of improved homogeneity for use in the production of relatively high refractive index polymeric compositions is described herein. Polymeric compositions so produced are useful in the production of ophthalmic devices such as for example intraocular lenses and corneal inlays. The preferred polymeric compositions are produced through the copolymerization of one or more polysiloxane prepolymers with hydrosilane-containing polysiloxanes.

27 Claims, No Drawings

PROCESS FOR THE PRODUCTION OF POLYSILOXANE-BASED POLYMERIC COMPOSITIONS FOR USE IN MEDICAL DEVICES

FIELD OF THE INVENTION

The present invention relates to an improved process for the production of polysiloxane-based polymeric compositions useful in the manufacture of biocompatible medical devices. More particularly, the present invention relates to an improved process for the production of polysiloxane-based polymeric compositions that eliminates difficulties experienced in preparing polysiloxane prepolymers to completion and difficulties experienced in the subsequent purification thereof.

BACKGROUND OF THE INVENTION

Since the 1940's optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. One such suitable class of soft, foldable materials is silicone elastomers fabricated through the polymerization of divinyl-end capped poly(dialkyl)-co-(diaromatic substituted) siloxane with polysiloxanes having multiple hydrosilane groups. This silicone elastomer producing polymerization reaction is achieved under thermal conditions using a platinum catalyst. A component added to the described siloxane and polysiloxanes prior to initiation of the polymerization reaction, is a reinforcing agent to enhance the mechanical properties of the silicone elastomer end product so fabricated. Examples of suitable reinforcing agents include a silica filler or an organic reinforcing resin such as polysiloxane with a vinyl functional group.

The prepolymer, divinyl-end capped poly(dialkyl)-co-(diaromatic substituted) siloxane used in the polymerization reaction described above, is prepared by reacting a 1,3-bisvinyl tetraalkyldisiloxane, a mixture of octamethyl cyclotetrasiloxane and an aromatic group containing cyclosiloxane, especially octaphenylcyclo-tetrasiloxane. Using an amine or a potassium silanoate as a catalyst, the reaction used to prepare the noted prepolymer is carried out at 40–100° C. in neat or in an organic solvent. This polymerization reaction only reaches an equilibrium with some cyclics, either those of the original components or those regenerated from the growing polymer, which then remain as side products. The resulting product was purified using a high temperature, high vacuum, thin film evaporator to remove solvent and volatile cyclics. Because of the poor solubility of the aromatic cyclics, incorporating a quantitative amount of the aromatic cyclics into the growing polymer molecule proved difficult. Likewise, due to high melting points, the aromatic cyclics have no vapor pressures and can not be removed using the thin film evaporator. As a result, in most cases, the aromatic cyclics remain as a contaminant in the final silicone elastomer product. The presence of aromatic cyclics as contaminants in the final silicone elastomer product creates the potential for defects and possible failures in products produced therefrom.

Because of the noted shortcomings in the quality of divinyl-end capped poly(dialkyl)-co-(diaromatic substituted) siloxane prepolymer using the described known process, there is a need to have an improved process for synthesizing the divinyl-end capped poly(dialkyl)-co-(diaromatic substituted) siloxane prepolymer.

SUMMARY OF THE INVENTION

Soft, foldable, high refractive index, high elongation, polymeric compositions or silicone elastomers are prepared in accordance with the present invention through the copolymerization of aromatic-substituted polysiloxane prepolymers with one or more polysiloxanes having multiple hydrosilane groups. The improved production process of the present invention eliminates difficulties formerly encountered in preparing polysiloxane prepolymers to completion as well as difficulties formerly encountered in the subsequent purification thereof. Following preparation of the polysiloxane prepolymers using the process of the present invention, the prepolymers are copolymerized with selected hydro-silane-containing polysiloxanes and other comonomers/components to form desirable polymeric compositions useful in the manufacture of biocompatible medical devices such as ophthalmic devices. Such desirable polymeric compositions are transparent, relatively high in strength for durability during surgical manipulation, relatively high in elongation, relatively high in refractive index and particularly well suited for use in the manufacture of ophthalmic devices such as intraocular lens (IOL) implants, contact lenses, keratoprostheses, corneal rings, corneal inlays and the like. Medical devices fabricated from the polymeric compositions or silicone elastomers produced using polysiloxane prepolymers prepared in accordance with the present invention are of improved product quality and reliability.

The process of the present invention is used to prepare divinyl-end capped poly(dialkyl)-co-(diaromatic substituted) siloxane prepolymers having a structure generally represented by Formula 1 below:

Formula 1

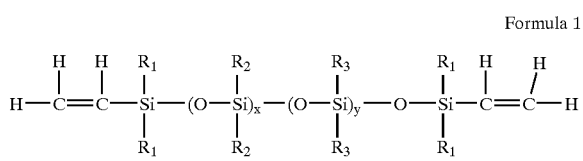

wherein the $R_1$ groups may be the same or different alkyl substituents or aromatic substituents; the $R_2$ groups may be the same or different alkyl substituents; the $R_3$ groups may be the same or different aromatic substituents; and x and y may be the same or different natural numbers so that $x/x+y$ is at least equal to 0.5 and each $OSi(R_2)_2$ and each $OSi(R_3)_2$ are independently and randomly distributed in the prepolymer molecule.

Accordingly, it is an object of the present invention to provide a process for the production of transparent, biocompatible polymeric compositions having desirable physical characteristics and relatively high refractive indices.

Another object of the present invention is to provide a process for the production of polymeric compositions having relatively high refractive indices and good clarity.

Another object of the present invention is to provide a process for the production of polymeric compositions suitable for use in the manufacture of ophthalmic devices.

Another object of the present invention is to provide a process for the production of polymeric compositions suitable for use in the manufacture of intraocular lens implants.

Still another object of the present invention is to provide a process for the production of polymeric compositions that are economical to produce.

These and other objectives and advantages of the present invention, some of which are specifically described and others that are not, will become apparent from the detailed description and claims that follow.

DETAILED DESCRIPTION OF THE INVENTION

The present invention relates to a novel process for the production of divinyl-terminated poly(dialkyl)-co-(diaromatic-substituted) siloxane prepolymers and the use of such prepolymers to produce biocompatible polymeric compositions having desirable physical properties and relatively high refractive indices for use in the manufacture of ophthalmic devices. The aromatic-substituted polysiloxane prepolymers of the present invention are represented generally by Formula 1 below:

Formula 1

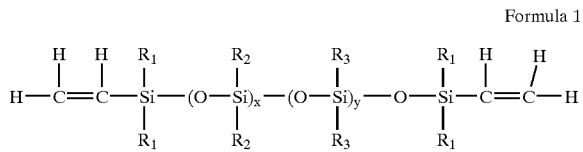

wherein the $R_1$ groups may be the same or different selected from the group consisting of $C_{1-10}$ alkyl substituents such as for example but not limited to methyl, propyl or octyl but preferably methyl to lower costs and $C_{6-30}$ aromatic substituents such as for example but not limited to phenyl or naphthyl; the $R_2$ groups may be the same or different $C_{1-10}$ alkyl substituents such as for example but not limited to methyl, propyl, or octyl but preferably methyl to lower costs; the $R_3$ groups may be the same or different $C_{6-30}$ aromatic substituents such as for example but not limited to phenyl or naphthyl; and x and y may be the same or different natural numbers so that $x/x+y$ is at least equal to 0.5 and each $OSi(R_2)_2$ and $OSi(R_3)_2$ are independently and randomly distributed in the prepolymer molecule such that the prepolymer molecular weight is at least approximately 1000 and refractive index is at least 1.42.

The polysiloxane prepolymers of Formula 1 above are produced using the process of the present invention through polymerization of dialkoxydialkyl silane (Component A or "A") represented generally by Formula 2 below, dialkoxy-diaromatic substituted silane (Component B or "B") represented generally by Formula 3 below and 1,3-bisvinyl tetraalkyldisiloxane (Component C or "C") represented generally by Formula 4 below.

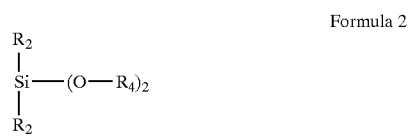

Formula 2

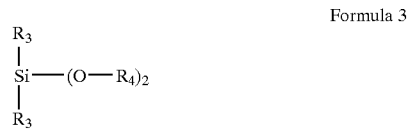

Formula 3

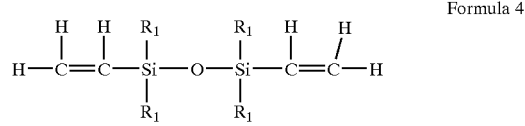

Formula 4 wherein $R_1$, $R_2$ and $R_3$ have the same definitions as those provided for the same with regard to Formula 1 above, and $R_4$ is selected from the group consisting of methyl and ethyl.

By using Components A, B and C in varying molar ratios, the refractive index and molecular weight of the polysiloxane prepolymer may be manipulated to achieve the particular properties desired. As the polymerization of Components A, B and C proceeds, the molecular weight grows until the reaction reaches equilibrium. A polysiloxane prepolymer of Formula 1 with cyclics side products in equilibrium therewith is thus produced. The cyclics side products contain mixtures of cyclics of dialkylsiloxane and diaromatic siloxane in random structure, with a total composition in proportion to that present in the amounts of Components A and B used. On average, each cyclics molecule has far lower aromatic content. While complicated in structure, the final cyclics side products in equilibrium with the polysiloxane prepolymer are more volatile under high vacuum than pure diaromatic siloxane cyclics and thus can be relatively easily separated from or removed from the polysiloxane prepolymer by wipe-film evaporator. As a result, the polysiloxane prepolymer so produced in accordance with the present invention is more homogeneous and thus is superior for use in the production of polymeric compositions for medical devices such as biocompatible ophthalmic devices. Other purification techniques such as preparative size exclusion chromatography (SEC), supercritical fluid (SCF) extraction or other techniques known to those skilled in the art of polymer chemistry can likewise be used in the purification of the subject polysiloxane prepolymers having been prepared in accordance with the process of the present invention.

Soft, foldable, relatively high refractive index of approximately 1.42 or greater, relatively high elongation of approximately 100 percent or greater, polymeric compositions are synthesized using one or more polysiloxane prepolymers produced through the process of the present invention. To produce the subject polymeric compositions, one or more polysiloxane prepolymers produced using the process of the present invention are copolymerized with a hydrosilane-containing polymer, and reinforcing components that are added to enhance the mechanical properties of the polymeric compositions so fabricated.

The hydro-silane containing polymer useful for copolymerization with the subject polysiloxane prepolymers, is generally represented by Formula 5 below.

Formula 5

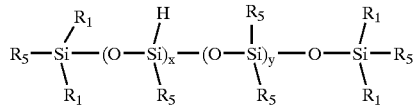

wherein $R_1$ has the same definition as that provided for $R_1$ of Formula 1 above; the $R_5$ groups may be the same or different selected from the group consisting of hydrogen and $C_{1-10}$ alkyl substituents such as for example but not limited to methyl, propyl, or octyl but preferably methyl to lower costs; and x and y may be the same or different natural numbers.

Suitable reinforcing components for use in the copolymerization of the polysiloxane prepolymer produced in accordance with the process of the present invention include but are not limited to a silicon filler or an organic resin such as for example a polysiloxane with multiple vinyl groups. However, regardless of which reinforcing agent is employed, the number of hydrosilane groups should be greater than or equal to the number of vinyl groups present in the final polymeric composition to be used in the manufacture of medical devices.

The polymeric compositions manufactured using polysiloxane prepolymers produced through the process of the present invention have refractive indices of approximately 1.42 or greater, relatively low glass transition temperatures of approximately 30 degrees Celsius or less and relatively high elongations of approximately 100 percent or greater. The polymeric compositions with the desirable physical properties described herein are particularly useful in the manufacture of ophthalmic devices such as but not limited to intraocular lenses (IOLs) and corneal inlays due to the increased homogeneity of the polysiloxane prepolymer.

IOLs having thin optic portions are critical in enabling a surgeon to minimize surgical incision size. Keeping the surgical incision size to a minimum reduces intraoperative trauma and postoperative complications. A thin IOL optic Portion is also critical for accommodating certain anatomical locations in the eye such as the anterior chamber and the ciliary sulcus. IOLs may be placed in the Anterior chamber for increasing visual acuity in both phakic and phakic eyes and placed in the ciliary sulcus for increasing visual acuity in phakic eyes.

The polymeric compositions produced as described herein have the flexibility required to allow ophthalmic devices manufactured from the same to be folded or deformed for insertion into an eye through the smallest possible surgical incision, i.e., 3.5 mm or smaller. It is unexpected that the subject polymeric compositions described herein could possess the ideal physical properties disclosed herein. The ideal physical properties of the subject polymeric compositions are unexpected because high refractive index monomers or copolymers typically lend to polymers that have increased crystallinity and decreased clarity, which does not hold true in the case of the subject polymeric compositions.

One or more suitable ultraviolet light absorbers may optionally be used in the manufacture of the subject polymeric compositions. Such ultraviolet light absorbers include for example but are not limited to 2-[3'-tert-butyl-5'-(3"-dimethylvinylsilylpropoxy)-2'-hydroxyphenyl]-5-methoxybenzotriazole or 2-(3'-allyl-2'-hydroxy-5'-methylphenyl)benztriazole.

The polymeric compositions made from polysiloxane prepolymers produced in accordance with the process of the present invention, having refractive indices of approximately 1.42 or greater and elongation of 100 percent or greater, are described in still greater detail in the examples that follow.

EXAMPLE 1

Preparation of Viny-end-capped Poly(dimethyl)-co-(diphenyl)siloxane

A 500-mL 3-neck round bottom flask was charged with 1,3-bis-vinyl tetramethydisiloxane (0.277 g), dimethydimethoxysilane (141.68 g) and diphenyidimethoxysilane (18.73 g). Then a mixture of water (21.95 g) and concentrated hydrochloric acid (15.2 mL) was added into the flask slowly. The contents were then refluxed for one hour at 60° C. while stirring with a mechanical stirrer. Methanol was then distilled, with 65 grams collected. Then, added to the residue was a 50/50 mixture of water and hydrochloric acid of equal volume. The same was then refluxed for 4 hours. The product was then dissolved and then extracted once with water, twice with 0, 5% sodium bicarbonate solution, once with saturated sodium chloride solution and once again with water. The same was then dried with magnesium sulfate. Next, the solution was filtered and the solvent removed. Finally, the residue was stripped under high vacuum at 70° C. overnight. The product was characterized by size exclusion chromatography (SEC). The high molecular weight portion (70.5%), Mn=6034, Mw=9,326. The low molecular weight portion (29.5%), Mn=331, Mw (356).

EXAMPLE 2

Purification of the Viny-end-capped Poly(dimethyl)-co-(diphenyl)siloxane of Example 1

The product from Example 1 was passed through a wipe-film evaporator under high vacuum (0.02 mmHg) and high temperature (220° C.). The cyclics residue was removed completely as shown by SEC.

EXAMPLE 3

Comparison of Diviny-end Capped Polydiemthy-co-diphenylsiloxane Made from Different Processes A purchased product having a 15–17% diphenylsiloxane content and having been fabricated from diphenylsiloxane cyclics, was compared to the product from Examples 1 and 2 above under microscope (30×). It was found that the purchased product produced from diphenylsiloxane cyclics had many irregular-shaped crystallites and strings of droplet-like defects. To the contrary, the product from Examples 1 and 2 above was clean, and the product from Example 1, even without stripping of cyclics, had no crystallites.

EXAMPLE 4

Preparation of Silicone Elastomers from the Product of Examples 1 and 2

A mixture containing a divinyl-capped polysiloxane prepolymer from Examples 1 and 2 above, a vinyl-capped polysiloxane reinforcing agent and a hydrosilane-containing polysilxane, a benzotriazole monomer and a platinum-silicone catalyst, is mixed well and air-bubbles removed. The mixture is then cured between two stainless steel plates covered with aluminum foil at 180° C. for 30 minutes. After release from the steel plates and aluminum foil, the elastomeric slab is observed under microscope. No crystallites or strings of droplet-like defects are observed.

Medical devices produced using polymeric compositions or silicone elastomers produced using the process of the present invention may be manufactured in accordance with methods known to those skilled in the art of the specific ophthalmic device being produced. For example, if an intraocular lens is to be produced, the same may be manufactured by methods known to those skilled in the art of intraocular lens production.

Ophthalmic devices such as but not limited to IOLs and corneal inlays manufactured using polymeric compositions produced using the process of the present invention can be of any design capable of being rolled or folded for implantation through a relatively small surgical incision, i.e., 3.5 mm or less. For example, intraocular implants such as IOLs comprise an optic portion and one or more haptic portions. The optic portion reflects light onto the retina and the permanently attached haptic portions hold the optic portion in proper alignment within an eye following implantation. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of the same polymeric composition produced using the process of the present invention. Alternatively however, the IOL optic portion and haptic portions may be manufactured from different materials and/or different formulations of polymeric compositions produced using the process of the present invention, such as described in detail in U.S. Pat. Nos. 5,217,491 and 5,326,506, each incorporated herein in their entirety by reference. Once the material(s) are selected, the same may be cast in molds of the desired shape, cured and removed from the molds. After such molding, the IOLs are then cleaned, polished, packaged and sterilized by customary methods known to those skilled in the art. Alternatively, rather than molding, the IOLs may be manufactured by casting said polymeric composition in the form of a rod; lathing or machining said rod into disks; and lathing or machining said disks into an ophthalmic device prior to cleaning, polishing, packaging and sterilizing the same.

In addition to IOLs, polymeric compositions produced using the process of the present invention are also suitable for use in the production of other ophthalmic devices such as contact lenses, keratoprostheses, capsular bag extension rings, corneal inlays, corneal rings and like devices.

Ophthalmic devices manufactured using polymeric compositions produced using the process of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While there is shown and described herein a process for producing polysiloxane prepolymers, and polymeric compositions and ophthalmic devices made from the subject polysiloxane prepolymers, it will be manifest to those skilled in the art that various modifications may be made without departing from the spirit and scope of the underlying inventive concept and that the same is not limited to particular processes and structures herein shown and described except insofar as indicated by the scope of the appended claims.

We claim:

1. A dialkoxydialkyl silane,

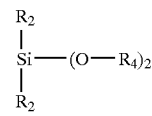

wherein the $R_2$ groups may be the same or different $C_{1-10}$ alkyl substituents and $R_4$ is selected from the group consisting of methyl and ethyl, copolymerized with a dialkoxydiaromatic substituted silane and a 1,3-bisvinyl tetraalkyldisiloxane, to produce polysiloxane prepolymers,

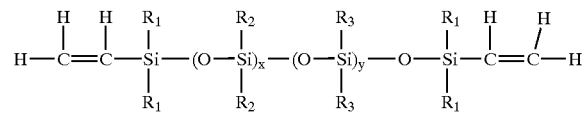

of increased homogeneity, wherein the $R_1$ groups may be the same or different selected from the group consisting of $C_{1-10}$ alkyl substituents and $C_{6-30}$ aromatic substituents; the $R_2$ groups may be the same or different $C_{1-10}$ alkyl substituents; the $R_3$ groups may be the same or different $C_{6-30}$ aromatic substituents; and x and y may be the same or different natural number with x/x+y at least equal to 0.5.

2. A dialkoxydiaromatic substituted silane,

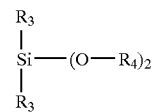

wherein the $R_3$ groups may be the same or different $C_{6-30}$ aromatic substituents and $R_4$ is selected from the group consisting of methyl and ethyl, copolymerized with a dialkoxydialkyl silane and a 1,3-bisvinyl tetraalkyldisiloxane, to produce polysiloxane prepolymers,

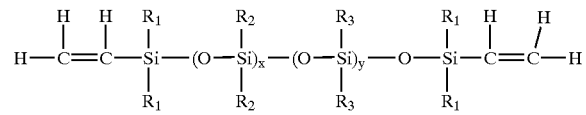

of increased homogeneity, wherein the $R_1$ groups may be the same or different selected from the group consisting of $C_{1-10}$ alkyl substituents and $C_{6-30}$ aromatic substituents; the $R_2$ groups may be the same or different $C_{1-10}$ alkyl substituents; the $R_3$ groups may be the same or different $C_{6-30}$ aromatic substituents; and x and y may be the same or different natural number with x/x+y at least equal to 0.5.

3. A 1,3-bisvinyl tetraalkyldisiloxane,

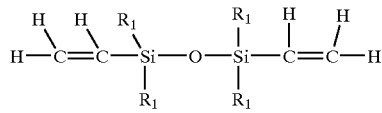

wherein the $R_1$ groups may be the same or different selected from the group consisting of $C_{1-10}$ alkyl substituents and $C_{6-30}$ aromatic substituents, copolymerized with a dialkoxydialkyl silane and a dialkoxydiaromatic substituted silane, to produce polysiloxane prepolymers,

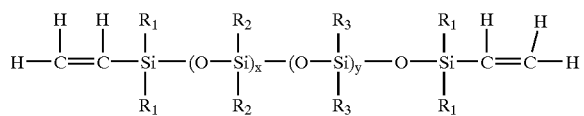

of increased homogeneity, wherein the $R_1$ groups may be the same or different selected from the group consisting of $C_{1-10}$ alkyl substituents and $C_{6-30}$ aromatic substituents; the $R_2$ groups may be the same or different $C_{1-10}$ alkyl substituents; the $R_3$ groups may be the same or different $C_{6-30}$ aromatic substituents; and x and y may be the same or different natural number with x/x+y at least equal to 0.5.

4. The polysiloxane prepolymers of claim 1, 2 or 3 wherein at least one of said $R_1$ groups is an aromatic substituent.

5. The polysiloxane prepolymers of claim 1, 2 or 3 wherein at least one of said $R_1$ groups is an alkyl substituent.

6. A polymeric composition produced through the copolymerization of one or more polysiloxane prepolymers of claim 1, 2 or 3 with one or more hydrosilane-containing polysiloxanes and a reinforcing component.

7. The polymeric composition of claim 6 wherein said one or more hydrosilane-containing polysiloxanes comprise:

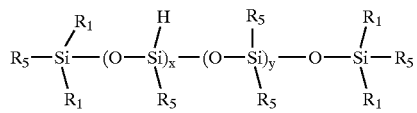

wherein the $R_1$ groups may be the same or different selected from the group consisting of $C_{1-10}$ alkyl substituents and $C_{6-30}$ aromatic substituents; the $R_5$ groups may be the same or different selected from the group consisting of hydrogen and $C_{1-10}$ alkyl substituents; and x and y may be the same or different natural number.

8. The polymeric composition of claim 6 wherein said reinforcing component is selected from a group consisting of a silica filler and a polysiloxane with multiple vinyl groups.

9. The polymeric composition of claim 6 wherein said reinforcing component is a silica filler.

10. The polymeric composition of claim 6 wherein said reinforcing component is a polysiloxane with multiple vinyl groups.

11. The polymeric composition of claim 6 wherein the number of hydrosilane groups is greater than or equal to the number of vinyl groups.

12. A process for producing polysiloxane prepolymers

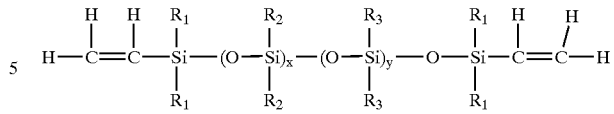

wherein the $R_1$ groups may be the same or different selected from the group consisting of $C_{1-10}$ alkyl substituents and $C_{6-30}$ aromatic substituents; the $R_2$ groups may be the same or different $C_{1-10}$ alkyl substituents; the $R_3$ groups may be the same or different $C_{6-30}$ aromatic substituents; and x and y may be the same or different natural number with x/x+y at least equal to 0.5, comprising:

polymerizing a dialkoxydialkyl silane, a dialkoxydiaromatic substituted silane and a 1,3-bisvinyl tetraalkyldisiloxane.

13. The process of claim 12 wherein said diakoxydialkyl silane comprises:

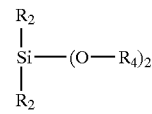

wherein the $R_2$ groups may be the same or different $C_{1-10}$ alkyl substituents and $R_4$ is selected from the group consisting of methyl and ethyl.

14. The process of claim 12 wherein said wherein said dialkoxydiaromatic substituted silane comprises:

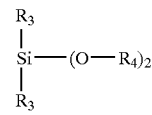

wherein the $R_3$ groups may be the same or different $C_{6-30}$ aromatic substituents and $R_4$ is selected from the group consisting of methyl and ethyl.

15. The process of claim 12 wherein said wherein said 1,3-bisvinyl tetraalkyldisiloxane comprises:

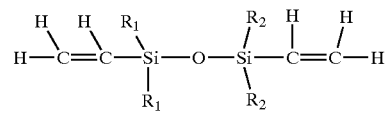

wherein the $R_1$ groups may be the same or different selected from the group consisting of $C_{1-10}$ alkyl substituents and $C_{6-30}$ aromatic substituents.

16. A process for producing a polymeric composition comprising:

polymerizing one or more polysiloxane prepolymers of claim 1, 2 or 3, a hydrosilane-containing polysiloxane and a reinforcing component.

17. The process of claim 16 wherein said one or more hydrosilane-containing polysiloxanes comprise:

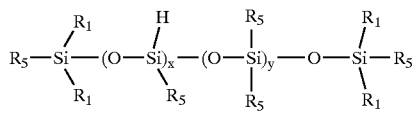

wherein the $R_1$ groups may be the same or different selected from the group consisting of $C_{1-10}$ alkyl substituents and $C_{6-30}$ aromatic substituents; the $R_5$ groups may be the same or different selected from the group consisting of hydrogen and $C_{1-10}$ alkyl substituents; and x and y may be the same or different natural number.

18. The process of claim 16 wherein said reinforcing component is selected from a group consisting of a silica filler or a polysiloxane with multiple vinyl groups.

19. The process of claim 16 wherein said reinforcing component is a silica filler.

20. The process of claim 16 wherein said reinforcing component is a polysiloxane with multiple vinyl groups.

21. The process of claim 16 wherein the number of hydrosilane groups is greater than or equal to the number of vinyl groups.

22. A method of producing an ophthalmic device using the polymeric composition produced through the process of claim 16 comprising casting said polymeric composition into a shaped body.

23. A method of producing an ophthalmic device using the polymeric composition produced through the process of claim 16 comprising:

casting said polymeric composition in the form of a rod;

lathing or machining said rod into disks; and lathing or machining said disks into an ophthalmic device.

24. A method of using the ophthalmic device produced through the method of claim 22 comprising:

making an incision in the cornea of an eye; and implanting said ophthalmic device.

25. A method of producing an ophthalmic device using a polymeric composition produced from one or more of the polysiloxane prepolymers of claim 1, 2 or 3 comprising:

pouring said polymeric composition prior to curing into a mold;

curing said polymeric composition; and removing said polymeric composition from said mold following curing thereof.

26. A method of using the ophthalmic device produced through the method of claim 25 comprising:

making an incision in the cornea of an eye; and implanting said ophthalmic device.

27. A method of using the ophthalmic device produced through the method of claim 23 comprising:

making an incision in the cornea of an eye; and implanting said ophthalmic device.

* * * * *